Figure 1:
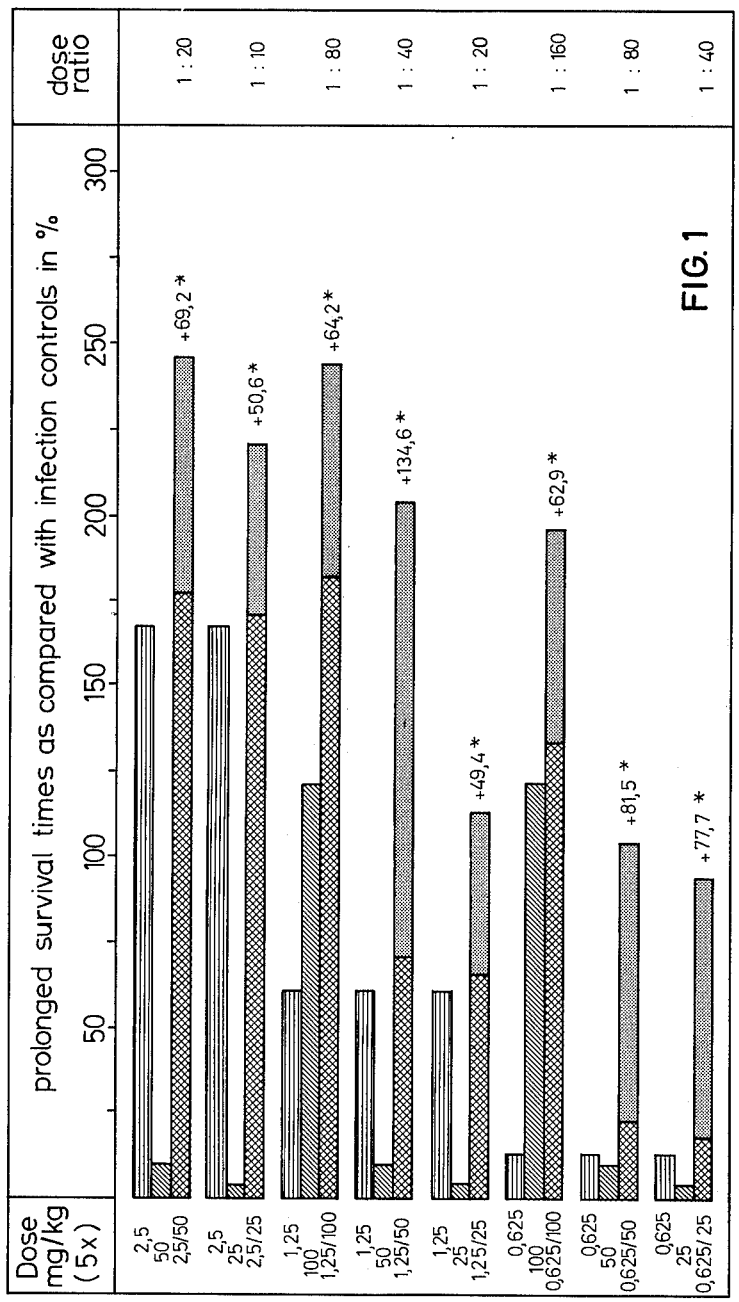

United States Patent [19]

Raether et al.

[11] 4,260,615
[45] Apr. 7, 1981

[54] ANTIMALARIAL COMPOSITIONS

[75] Inventors: Wolfgang Raether, Dreieich; Walter Dürckheimer, Hattersheim am Main; Hans Seidenath, Bad Nauheim, all of Fed. Rep. of Germany

[73] Assignee: Hoechst Aktiengesellschaft, Frankfurt am Main, Fed. Rep. of Germany

[21] Appl. No.: 954,900

[22] Filed: Oct. 26, 1978

[30] Foreign Application Priority Data

Oct. 28, 1977 [DE] Fed. Rep. of Germany ....... 2748333

[51] Int. Cl.³ .................... A61K 31/435; A61K 31/47
[52] U.S. Cl. .................................. 424/257; 424/258; 424/229
[58] Field of Search ................................ 424/257, 258

[56] References Cited
PUBLICATIONS

The Merck Index, 8th ed., 1968, Merck & Co., Inc., Rahway, N.J., p. 247
Chemical Abstracts, 83:9827w (1975).

Primary Examiner—Jerome D. Goldberg
Attorney, Agent, or Firm—Curtis, Morris & Safford

[57] ABSTRACT

Antimalarial compositions are disclosed containing as the active ingredient a mixture of a tetrahydroacridone of the general formula I

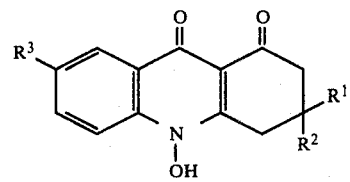

in which
$R^1$ represents methyl, phenyl, p-chlorophenyl, m-chlorophenyl, p-fluorophenyl, p-trifluoromethylphenyl, o-trifluoromethylphenyl or o-chloro-p-trifluoromethylphenyl,
$R^2$ represents hydrogen or methyl, and
$R^3$ represents fluorine or chlorine, or a salt of such a compound with a physiologically compatible acid or base, with
(a) 6-methoxy-α-(5-vinyl-2-quinuclidinyl)-4-quinolinemethanol (Quinine),
(b) 7-chloro-4-(diethylamino-1-methyl-butylamino)-quinoline (Chloroquine),
(c) α-(2-piperidyl)-2,8-bis(trifluoromethyl)-4-quinolinemethanol (Mefloquine),
(d) 8-(4-amino-1-methylbutylamino)-6-methoxy-quinoline (Primaquine),
(e) 2,4-diamino-5-p-chlorophenyl-6-ethylpyrimidine (Pyrimethamine),
(f) 4,6-diamino-1-(p-chlorophenyl)-1,2-dihydro-2,2-dimethyl-s-triazine (Cycloguanil),
(g) 2,4-diamino-5-(3,4,5-trimethoxybenzyl)-pyrimidine (Trimethoprim),
(h) N'-(5,6-dimethoxy-4-pyrimidyl)-sulfanilamide (Sulfadoxine), or
(i) 4,4'-diaminodiphenylsulfone (Dapsone), or with a salt of a compound sub (a) to (i), with a physiologically compatible acid or base, the mixtures being in a proportion by weight of between 25:1 and 1:300 (tetrahydroacridone to compound sub (a) to (i)) in admixture with a pharmaceutically acceptable carrier and/or adjuvant.

3 Claims, 9 Drawing Figures

ANTIMALARIAL COMPOSITIONS

Eradication programms against malaria are conducted either by medicamentous prophylaxis in man or by using insecticides against the natural vectors (mosquitos of Anopheles Species).

However, the repeated use of antimalarials such as Chloroquine, which is often employed in prophylactic and curative treatment of malaria and which is relatively well tolerated, induce high resistance in the most pathogenic malaria species of man, Plasmodium falciparum. Even when using higher doses in an amount which is already in the toxic range, drug-resistant parasites can no longer be kept under control. Other human malaria strains, e.g. Plasmodium vivax, also show resistance to various known antimalarial drugs such as Pyrimethamine or other folic acid reductase inhibitors.

German Offenlegungsschrift No. 23 37 474 describes chemotherapeutically active tetrahydroacridone compounds which exhibit a high activity against various drug-sensitive malaria species, and also against Chloroquine- and other drug-resistant lines of Plasmodium berghei in mice. These lines are not influenced by known antimalarials such as 4-amino-quinoline derivatives or pyrimethamine.

Now, we have found a composition which is active against malaria and which is characterized by a content of a tetrahydroacridone of the general formula I

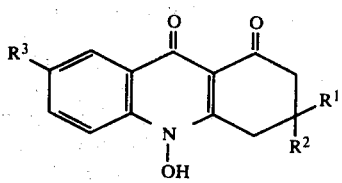

in which
$R^1$ represents methyl, phenyl, p-chlorophenyl, m-chlorophenyl, p-fluorophenyl, p-trifluoromethylphenyl, o-trifluoromethylphenyl or o-chloro-p-trifluoromethylphenyl,
$R^2$ represents hydrogen or methyl, and
$R^3$ represents fluorine or chlorine,
or a salt of such a compound with a physiologically compatible acid or base, with (a) 6-methoxy-α-(5-vinyl-2-quinuclidinyl)-4-quinolinemethanol (Quinine),
(b) 7-chloro-4-(diethylamino-1-methyl-butylamino)-quinoline (Chloroquine),
(c) α-(2-piperidyl)-2,8-bis(trifluoromethyl)-4-quinolinemethanol (Mefloquine),
(d) 8-(4-amino-1-methylbutylamino)-6-methoxy-quinoline (Primaquine),
(e) 2,4-diamino-5-p-chlorophenyl-6-ethylpyrimidine (Pyrimethamine),
(f) 4,6-diamino-1-(p-chlorophenyl)-1,2-dihydro-2,2-dimethyl-s-triazine (Cycloguanil),
(g) 2,4-diamino-5-(3,4,5-trimethoxybenzyl)-pyrimidine (Trimethoprim),
(h) N'-(5,6-dimethoxy-4-pyrimidyl)-sulfanilamide (Sulfadoxine), or
(i) 4,4'-diaminodiphenylsulfone (Dapsone),
or with a salt of a compound sub (a) to (i), with a physiologically compatible acid or base, the mixtures being in a proportion by weight of between 25:1 and 1:300 (tetrahydroacridone to compound sub (a) to (i)) in admixture with a pharmaceutically acceptable carrier and/or adjuvant.

Among the tetrahydroacridones of the general formula I, the following are particularly preferred:
3,3-dimethyl-7-fluoro-10-hydroxy-1-oxo-1,2,3,4-tetrahydro-9(10H)-acridone,
7-chloro-3,3-dimethyl-10-hydroxy-1-oxo-1,2,3,4-tetrahydro-9(10H)-acridone,
7-chloro-10-hydroxy-1-oxo-3-phenyl-1,2,3,4-tetrahydro-9-(10H)-acridone,
7-chloro-3-(4-chlorophenyl)-10-hydroxy-1-oxo-1,2,3,4-tetrahydro-9(10H)-acridone,
7-chloro-3-(3-chlorophenyl)-10-hydroxy-1-oxo-1,2,3,4-tetrahydro-9(10H)-acridone,
7-chloro-3-(4-fluorophenyl)-10-hydroxy-1-oxo-1,2,3,4-tetrahydro-9(10H)-acridone,
7-chloro-10-hydroxy-1-oxo-3-(2-trifluoromethylphenyl)-1,2,3,4-tetrahydro-9(10H)-acridone,
7-chloro-3-(2-chloro-4-trifluoromethylphenyl)-10-hydroxy-1-oxo-1,2,3,4-tetrahydro-9(10H)-acridone,
7-chloro-10-hydroxy-1-oxo-3-(4-trifluoromethylphenyl)-1,2,3,4-tetrahydro-9(10H)-acridone.

Among these tetrahydroacridones, the 4-chlorophenyl compound and the 2-chloro-4-trifluoromethyl-phenyl compound are especially active. The 4-trifluoromethylphenyl compound is particularly advantageous.

Depending on the type of the second antimalarial used with the tetrahydroacridones, the preferred proportions by weight used vary. When using Floxacrine in admixture with Quinine, a ratio of 1:10 to 1:160, in particular from 1:40 to 1:80; in admixture with Chloroquine from 4:1 to 1:20, in particular 2:1 to 1:8; in admixture with Mefloquine from 1:1.25 to 1:10; in admixture with Primaquine from 1:1.25 to 1:20, in particular 1:2.5 to 1:20; in admixture with Pyrimethamine from 21:1 to 1:1.5, in particular 10.4:1 to 1:1.5; in admixture with Cycloguanil from 1:35 to 1:284, in particular 1:142 to 1:284; in admixture with Trimethroprim from 1:10 to 1:80, in particular 1:40 to 1:80; in admixture with Sulfadoxine from 1:1 L to 1:32, in particular 1:1 to 1:6; in admixture with Dapsone from 1:5 to 1:80, in particular 1:10 to 1:80, the best synergistic was obtained.

The quantities of the composition to be administered vary corresponding to the individual activity of the components used. In the treatment of rodent malaria (P. berghei), mixtures of Floxacrine with Quinine, Cycloguanil, Trimethoprim or Dapsone give favourable results if they are given orally in a total dose, per administration, of 7.5–178 mg/kg, preferably 26.25–102.5 mg/kg. On the other hand, mixtures of Floxacrine and Chloroquine, Mefloquine, Primaquine, Pyrimethamine or Sulfadoxine are already active in total doses of between 1:37 and 21.25 mg/kg per administration, preferably between 1.56 and 11.25 mg/kg.

The treatment of patients suffering from malaria by administering a composition according to the invention being a potentiating combination of antimalarials is superior to the treatment with a mono-drug, because the emergence of resistance to either component is greatly slowed down and because toxicity is reduced markedly.

The compositions of the invention have an antimalarial action at essentially smaller doses than those of the individual components and also show, as proved with test animals, longer survival times than those of animals treated with the individual components. Drug-resistant P. berghei strains, for example a Chloroquine-resistant line of P. berghei, are well influenced espcially by a combination of Floxacrine with Chloroquine owing to the synergistic action of the individual components.

The physiological compatibility compositions according to the invention is good.

The compositions according to the invention may be administered per os or parenterally in doses ranging from 5 to 50 mg/kg body weight. As antimalarial drugs, dosage unit forms such as dragées or capsules for oral administration or ampoules for injections, each containing of from 50 to 200 mg of a mixture of active substances, are preferred. Such dosage units are generally administered once to three times, eventually fife times, daily depending on the condition of the patient.

For oral administration, there may be used in particular tablets, dragées, capsules, powders or granules, which contain the mixture of the active substances together with the usual excipients and adjuvants such as starch, cellulose powder, talcum, magnesium stearate, sugar, gelatin, calcium carbonate, finely divided silicic acid, carboxymethyl cellulose or similar substances.

For parenteral administration, in particular for intramuscular injections, there may be used sterile suspensions, for example oily suspensions prepared with the use of fatty oils such as olive oil, sesame oil, peanut oil, castor oil or a synthetic triglyceride, optionally with simultaneous use of surface-active agents such as sorbitane fatty acid esters. Furthermore, aqueous suspensions may be prepared, for example, with the use of ethoxylated sorbitane fatty acid esters, optionally with addition of thickeners such as polyethylene glycol or carboxymethyl cellulose.

To test the efficiency of the antimalarial compositions according to the invention, aqueous suspensions thereof are administered to mice by using an esophagal sound. For this purpose, the antimalarials are dissolved in water or in another suitable solvent or suspended in 2% aqueous Tylose suspension by adding 100 mg of the composition to be tested to 1 ml of the Tylose suspension. The concentration of active substances to be tested is adjusted by the addition of water. A dose of 0.5 ml per mouse per 20 g body weight was found to be advantageous. Prior to administration, the suspensions are treated by ultra-sound to attain a uniform dispersion of the active substances.

The following test report demonstrates the superiority of the use of compositions of the antimalarials according to the invention over the treatment with a mono-drug. Thus, when combinations of Floxacrine and antimalarials according to the invention are administered in special weight ratios to infected animals, there is observed a synergistic effect. As parameter for this effect there is taken the prolonged survival time in percent (%). The accompanying tables 1 to 9 and the figures 1 to 9 illustrate this effect more precisely. In column 4 of tables 1 to 9 there are listed the survival times, expressed in days post infectionem, of 10 infected animals treated with the individual components and with the combinations according to the invention and that of untreated infected control animals. In column 5 of tables 1-9, the mean and standard deviation of survival time of the infected and treated animals after the use of the individual components and of the combinations according to the invention and that of untreated infected control animals can be seen. In column 6 of tables 1-9 there are listed the means of the prolonged survival time, which are obtained when the mean of the survival time of the untreated infected control animals is subtracted from the mean of survival time of treated and infected animals after the use of the individual components and of the combinations according to the invention. To determine the synergistic effect the sum of the prolonged survival times after the use of the individual components is substracted from that obtained after the use of the combinations according to the invention (see FIGS. 1-9).

In the accompanying FIGS. 1 to 9 there are shown in illustrative manner the prolonged survival times in % after the use of the individual components and of the combinations according to the invention. These values expressed in percent were calculated from the means of survival time listed in column 6 of tables 1-9. The synergistic effect is obvious. The following legend applies to the FIGS. 1 to 9:

| | |
|---|---|
| ▓▓▓ | survival time (s.t.) Floxacrine (1) |
| ▓▓▓ | s.t. second component (2) |
| ▓▓▓ | s.t. after combination of (1) and (2) |
| ▓▓▓ | section of additive effect [s.t. (1) + s.t. (2)] |
| ▓▓▓ | section of synergistic effect = prolonged survival time |

The tests were run with a drug-sensitive strain of *Plasmodium berghei* (K 173, Vincke and Lips, 1048) on the one hand and a Chloroquine-resistant line of this strain on the other hand. Female and male NMRI mice, weighing 18 to 20 g, were kept in Makrolon ® cages of type I at constant temperature of 21° C. and a relative humidity of 65%. They were fed with Altromin ® and with water ad libitum. Approximately $6 \times 10^6$ parasitized erythrocytes of *P. berghei*, which had been adjusted to the adequate density by counting in a counting chamber and by suspension in physiological NaCl solution, were injected intraperitoneally to each mouse. To control the infection and the parasitemia course, blood films were made from tail blood of treated and infected animals and of untreated, infected animals three times a week, starting on D+6 (6 days after infection) until D+28. The blood films were stained with Giemsa stain and examined microscopically. Untreated animals died within 6 to 14 days post infectionem. The range of survival time of the infected controls can be attributed to the normal biological behaviour of the host-parasite relationship and technical errors occuring during counting of parasites and infection of animals. The treated, infected mice and the untreated, infected mice were inspected twice daily from D 0 (day of infection) until D+28 (termination of trial).

Animals were treated orally by using an esophagal sound. The first treatment was 2 hours, the second 1 day, the third 2 days, the forth 3 days and the fifth 4 days after infection (+2h, D+1, D+2, D+3, D+4). The same dose of the individual component or with the combination was given to a group of at least 10 animals. The action on the asexual blood stages of *P. berghei* of the compounds according to the invention was measured by the values of survival time in days after infection listed in tables 1 to 9 which were then transformed in percentage values in FIGS. 1-9. Animals which survived 28 days after infection and show no parasites in blood films per 10.000 erythrocytes were considered as cured. All trials were terminated on D+28.

TABLE 1

Synergistic action (over-additive section of the survival time in % - cf. FIG. 1) on blood forms of *Plasmodium berghei* (drug-sensitive strain) after application of compositions containing Floxacrine and Quinine sulfate in the NMRI mouse

| Preparation | dose mg/kg (5 ×) | dose ratio | observed values | | | | | | | | | | | $\bar{x}$, s | prolonged s.t. $\bar{x}$(prep.) - $\bar{x}$(IC) |
|---|---|---|---|---|---|---|---|---|---|---|---|---|---|---|---|
| Floxacrine | 2.5 | | 14 | 14 | 15 | 17 | 17 | 28 | 28 | 28 | 28 | 28 | 21.7 ± 6.7 | 13.6 |
| | 1.25 | | 9 | 10 | 12 | 12 | 13 | 14 | 14 | 14 | 16 | 16 | 13 ± 2.3 | 4.9 |
| | 0.625 | | 8 | 8 | 8 | 9 | 9 | 9 | 9 | 10 | 10 | 11 | 9.1 ± 1.1 | 1 |
| Quinine sulfate | 100 | | 13 | 13 | 15 | 15 | 19 | 19 | 20 | 21 | 22 | 22 | 17.9 ± 3.6 | 9.8 |
| | 50 | | 8 | 8 | 8 | 8 | 9 | 9 | 9 | 9 | 10 | 10 | 8.8 ± 0.8 | 0.7 |
| | 25 | | 8 | 8 | 8 | 8 | 8 | 8 | 9 | 9 | 9 | 9 | 8.4 ± 0.5 | 0.3 |
| Floxacrine and Quinine sulfate | 2.5/50 | 1:20 | 28 | 28 | 28 | 28 | 28 | 28 | 28 | 28 | 28 | 28 | 28 ± 0 | 19.9 |
| | 2.5/25 | 1:10 | 17 | 20 | 28 | 28 | 28 | 28 | 28 | 28 | 28 | 28 | 26.1 ± 4.1 | 18 |
| | 1.25/100 | 1:80 | 28 | 28 | 28 | 28 | 28 | 28 | 28 | 28 | 28 | 28 | 28 ± 0 | 19.9 |
| | 1.25/50 | 1:40 | 19 | 19 | 21 | 23 | 25 | 27 | 28 | 28 | 28 | 28 | 24.6 ± 3.8 | 16.5 |
| | 1.25/25 | 1:20 | 16 | 16 | 16 | 16 | 17 | 17 | 18 | 18 | 19 | 20 | 17.3 ± 1.4 | 9.2 |
| | 0.625/100 | 1:160 | 19 | 19 | 22 | 23 | 24 | 24 | 26 | 27 | 28 | 28 | 24 ± 3.3 | 15.9 |
| | 0.625/50 | 1:80 | 10 | 11 | 12 | 12 | 16 | 16 | 19 | 20 | 24 | 24 | 15.4 ± 5.2 | 8.3 |
| | 0.625/25 | 1:40 | 12 | 12 | 12 | 12 | 15 | 15 | 19 | 19 | 20 | 21 | 15.7 ± 3.7 | 7.6 |
| untreated, infected control animals | — | — | 7 | 8 | 8 | 8 | 8 | 8 | 8 | 8 | 9 | 9 | 8.1 ± 0.1 | — |

TABLE 2

Synergistic action (over-additive section of the survival time in % - cf. FIG. 2) on blood forms of *Plasmodium berghei* (drug-sensitive strain) after application of compositions containing Floxacrine and Chloroquine in the NMRI mouse

| Preparation | dose mg/kg (5 ×) | dose ratio | observed values | | | | | | | | | | | $\bar{x}$, s | prolonged s.t. $\bar{x}$(prep.) - $\bar{x}$(IC) |
|---|---|---|---|---|---|---|---|---|---|---|---|---|---|---|---|
| Floxacrine | 5 | | 14 | 15 | 18 | 18 | 28 | 28 | 28 | 28 | 28 | 28 | 23.3 ± 6.2 | 13.9 |
| | 2.5 | | 11 | 12 | 12 | 12 | 12 | 12 | 13 | 13 | 13 | 17 | 12.7 ± 1.6 | 3.3 |
| | 1.25 | | 9 | 9 | 11 | 11 | 11 | 11 | 11 | 11 | 14 | 14 | 11.2 ± 1.7 | 1.8 |
| Chloroquine (diphosphate) | 5 | | 9 | 9 | 9 | 9 | 10 | 10 | 10 | 10 | 13 | 14 | 10.3 ± 1.8 | 0.9 |
| | 2.5 | | 10 | 10 | 10 | 10 | 10 | 10 | 10 | 10 | 11 | 11 | 10.2 ± 0.4 | 0.8 |
| | 1.25 | | 9 | 9 | 9 | 9 | 9 | 9 | 9 | 10 | 10 | 10 | 9.3 ± 0.5 | −0.1 |
| | 0.62 | | 8 | 8 | 9 | 9 | 9 | 9 | 9 | 9 | 11 | 11 | 9.2 ± 1.0 | −0.2 |
| Floxacrine/ Chloroquine | 5/5 | 1:1 | 28 | 28 | 28 | 28 | 28 | 28 | 28 | 28 | 28 | 28 | 28 ± 0 | 18.6 |
| | 5/2.5 | 2:1 | 28 | 28 | 28 | 28 | 28 | 28 | 28 | 28 | 28 | 28 | 28 ± 0 | 18.6 |
| | 5/1.25 | 4:1 | 28 | 28 | 28 | 28 | 28 | 28 | 28 | 28 | 28 | 28 | 28 ± 0 | 18.6 |
| | 2.5/5 | 1:2 | 28 | 28 | 28 | 28 | 28 | 28 | 28 | 28 | 28 | 28 | 28 ± 0 | 18.6 |
| | 2.5/2.5 | 1:1 | 28 | 28 | 28 | 28 | 28 | 28 | 28 | 28 | 28 | 28 | 28 ± 0 | 18.6 |
| | 2.5/1.25 | 2:1 | 28 | 28 | 28 | 28 | 28 | 28 | 28 | 28 | 28 | 28 | 28 ± 0 | 18.6 |
| | 2.5/0.62 | 4:1 | 13 | 13 | 17 | 17 | 19 | 19 | 20 | 20 | 23 | 23 | 18.4 ± 3.5 | 9 |
| | 1.25/5 | 1:4 | 28 | 28 | 28 | 28 | 28 | 28 | 28 | 28 | 28 | 28 | 28 ± 0 | 18.6 |
| | 1.25/2.5 | 1:2 | 15 | 15 | 28 | 28 | 28 | 28 | 28 | 28 | 28 | 28 | 25.4 ± 5.5 | 16 |
| | 1.25/1.25 | 1:1 | 13 | 13 | 13 | 13 | 15 | 15 | 16 | 16 | 28 | 28 | 17 ± 5.9 | 7.6 |
| untreated, infected control animals | — | — | 7 | 7 | 9 | 9 | 9 | 9 | 9 | 10 | 12 | 13 | 9.4 ± 1.9 | — |

TABLE 2a

Figure 2:
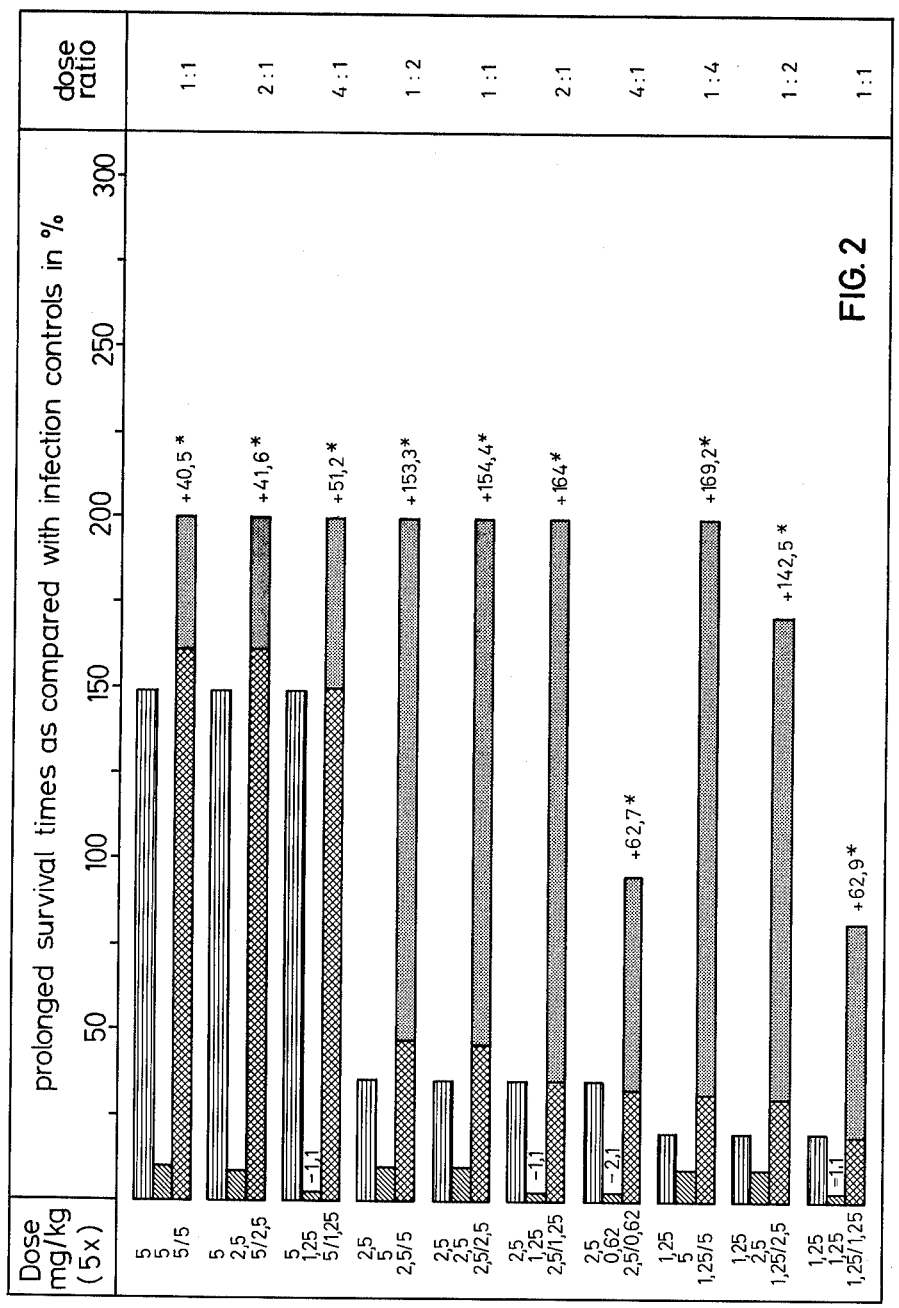
Figure 2A:
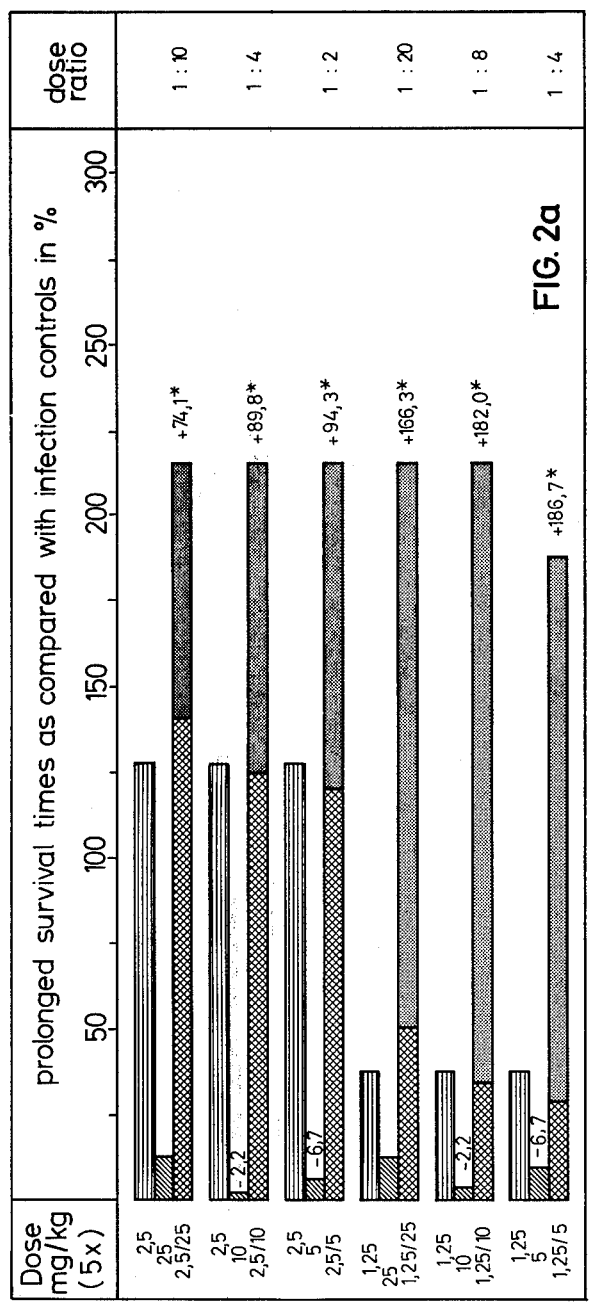
Figure 3:
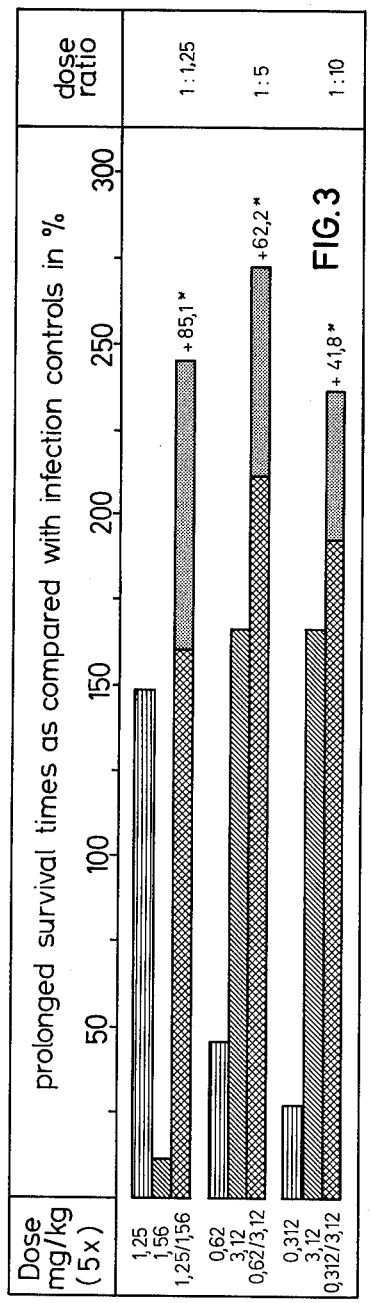
Figure 4:
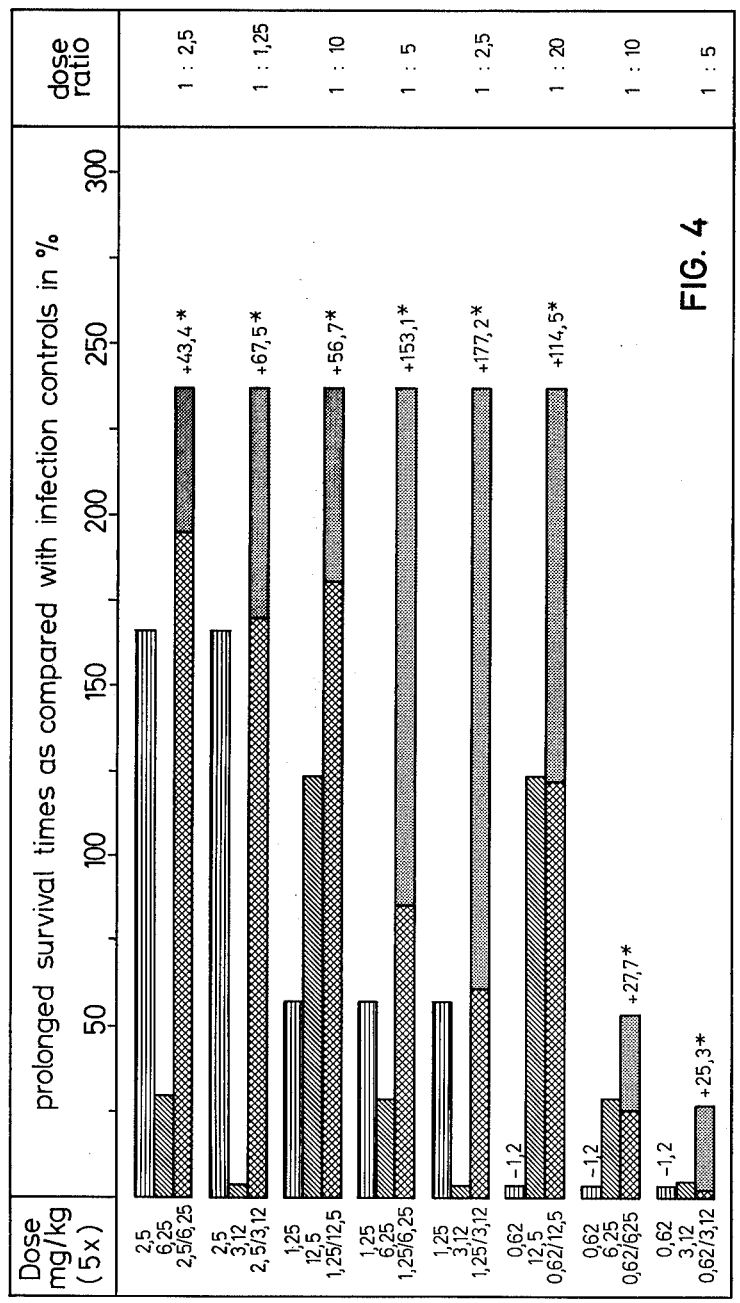
Figure 5:
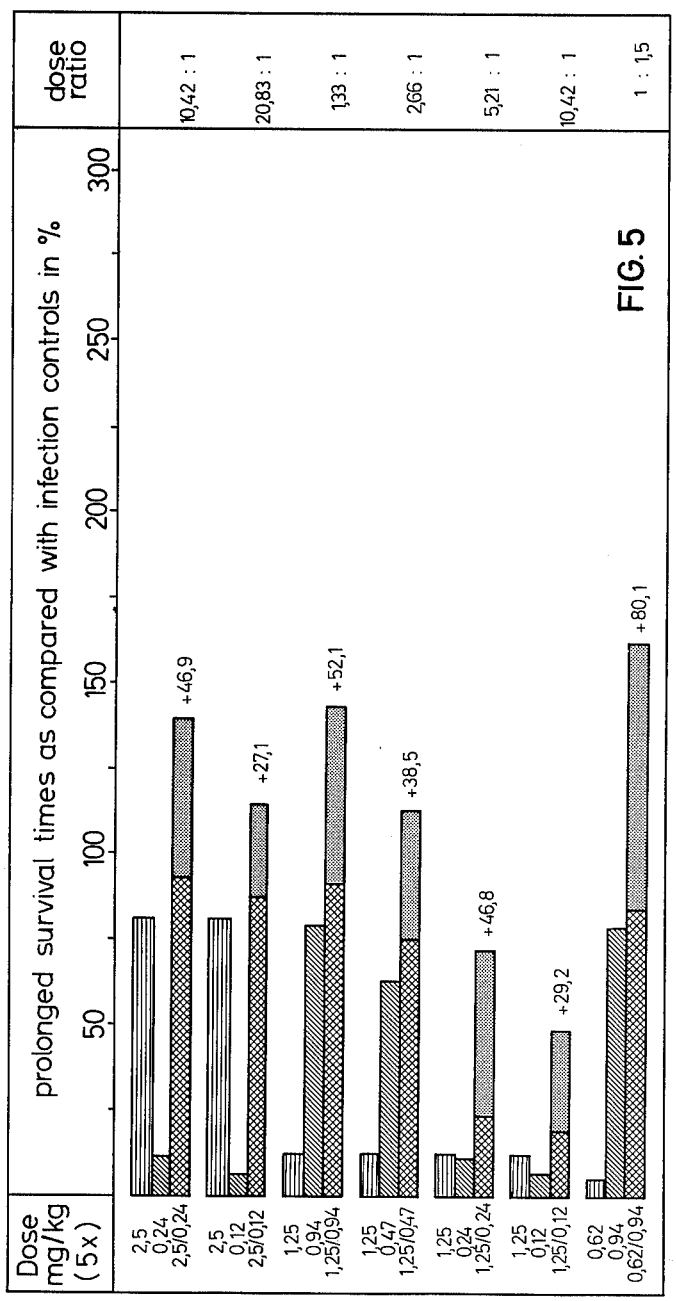
Figure 6:
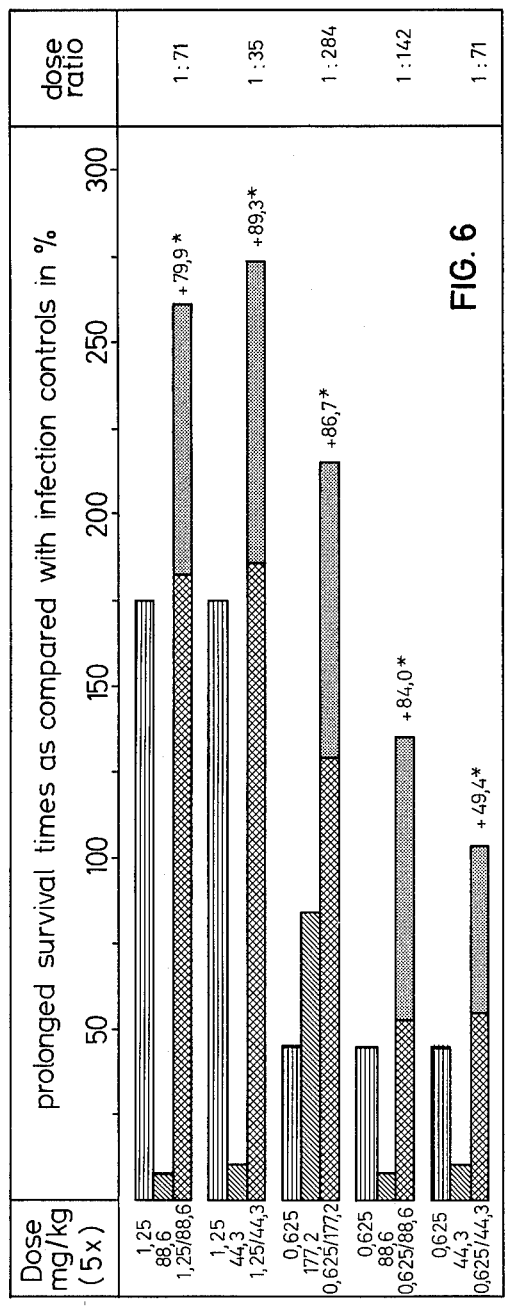
Figure 7:
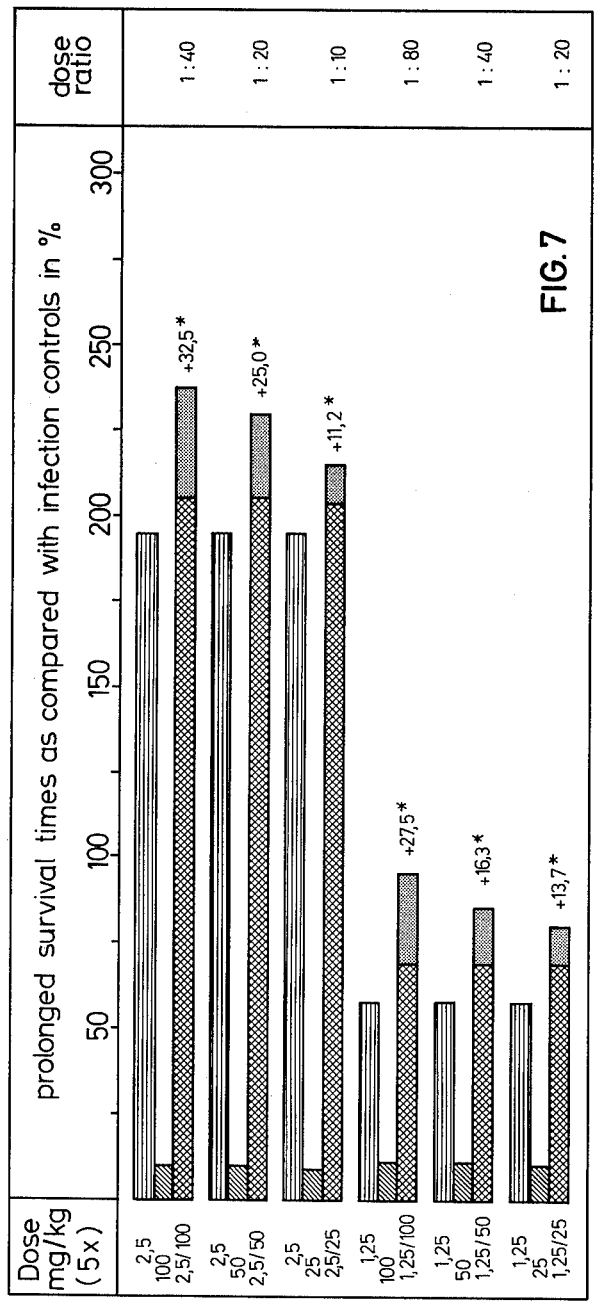
Figure 8:
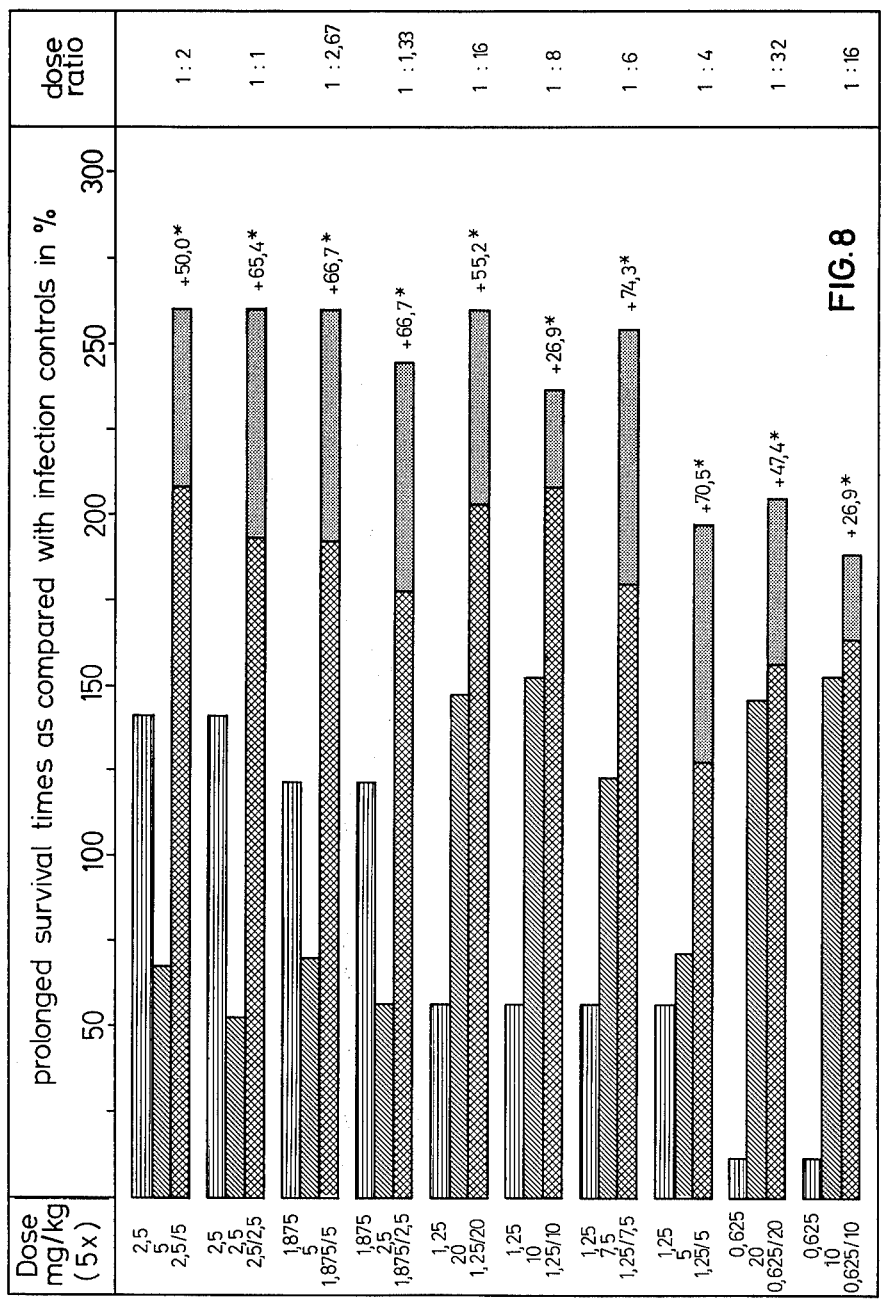
Figure 9:
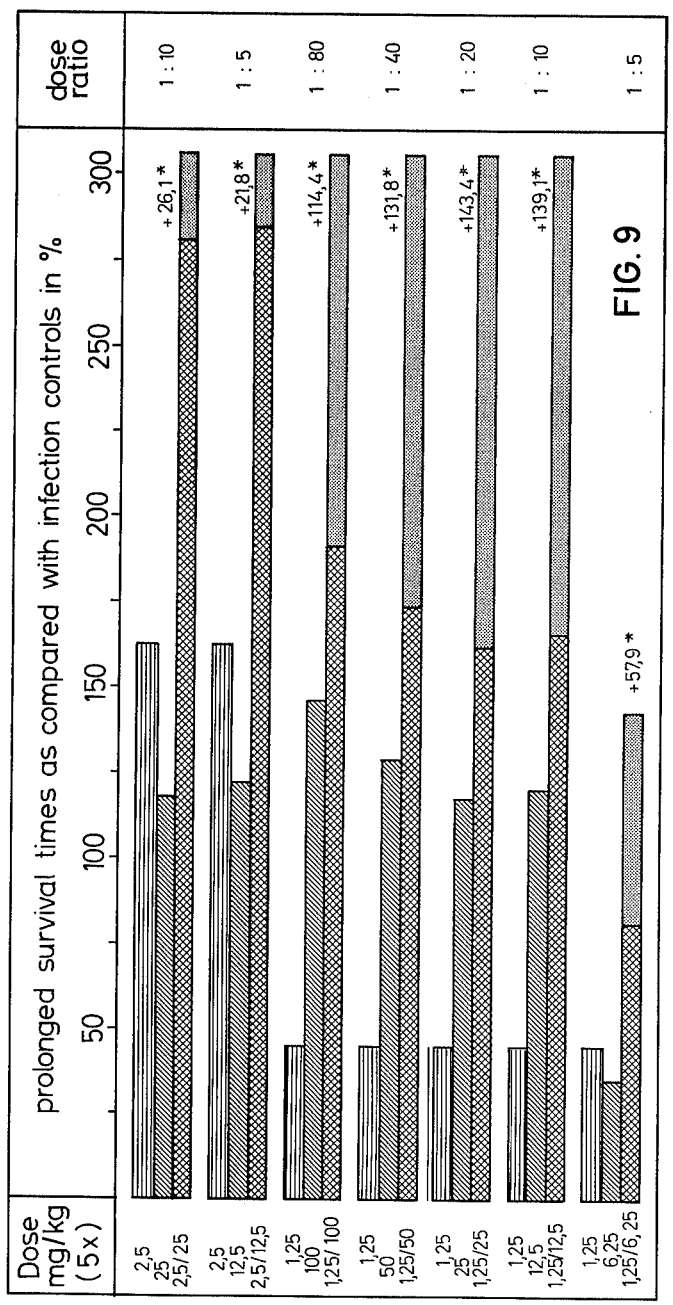

Synergistic action (over-additive section of the survival time in % - cf. FIG. 2a) on blood forms of *Plasmodium berghei* (drug-sensitive strain) after application of compositions containing Floxacrine and Chloroquine in the NMRI mouse

| Preparation | dose mg/kg (5 ×) | dose ratio | observed values | | | | | | | | | | | $\bar{x}$, s | prolonged s.t. $\bar{x}$(prep.) - $\bar{x}$(IC) |
|---|---|---|---|---|---|---|---|---|---|---|---|---|---|---|---|
| Floxacrine | 2.5 | | 13 | 13 | 15 | 15 | 17 | 17 | 28 | 28 | 28 | 28 | 20.2 ± 6.8 | 11.3 |
| | 1.25 | | 8 | 8 | 13 | 13 | 13 | 13 | 13 | 13 | 13 | 13 | 12 ± 2.1 | 3.1 |
| Chloroquine (diphosphate) | 25 | | 7 | 7 | 8 | 8 | 9 | 10 | 12 | 13 | 13 | 14 | 10.1 ± 2.7 | 1.2 |
| | 10 | | 6 | 6 | 7 | 8 | 8 | 9 | 10 | 10 | 10 | 13 | 8.7 ± 2.2 | −0.2 |
| | 5 | | 6 | 6 | 7 | 7 | 7 | 8 | 9 | 10 | 10 | 13 | 8.3 ± 2.2 | −0.6 |
| Floxacrine/ Chloroquine | 2.5/25 | 1:10 | 28 | 28 | 28 | 28 | 28 | 28 | 28 | 28 | 28 | 28 | 28 ± 0 | 19.1 |
| | 2.5/10 | 1:4 | 28 | 28 | 28 | 28 | 28 | 28 | 28 | 28 | 28 | 28 | 28 ± 0 | 19.1 |
| | 2.5/5 | 1:2 | 28 | 28 | 28 | 28 | 28 | 28 | 28 | 28 | 28 | 28 | 28 ± 0 | 19.1 |
| | 1.25/25 | 1.20 | 28 | 28 | 28 | 28 | 28 | 28 | 28 | 28 | 28 | 28 | 28 ± 0 | 19.1 |
| | 1.25/10 | 1:8 | 28 | 28 | 28 | 28 | 28 | 28 | 28 | 28 | 28 | 28 | 28 ± 0 | 19.1 |
| | 1.25/5 | 1:4 | 14 | 14 | 23 | 24 | 28 | 28 | 28 | 28 | 28 | 28 | 24.3 ± 5.7 | 15.4 |
| untreated, infected control | — | — | 6 | 6 | 6 | 6 | 9 | 10 | 10 | 10 | 13 | 13 | 8.9 ± 2.8 | — |

TABLE 2a-continued

Synergistic action (over-additive section of the survival time in % - cf. FIG. 2a) on blood forms of *Plasmodium berghei* (drug-sensitive strain) after application of compositions containing Floxacrine and Chloroquine in the NMRI mouse

| Preparation | dose mg/kg (5 ×) | dose ratio | action on blood forms of *P.berghei*, measured in survival times (s.t.) (days post infectionem) observed values | x̄, s | prolonged s.t. x̄(prep.) - x̄(IC) |
|---|---|---|---|---|---|
| animals | | | | | |

TABLE 3

Synergistic action (over-additive section of the survival time in % - cf. FIG. 3) on blood forms of *Plasmodium berghei* (drug-sensitive strain) after application of compositions containing Floxacrine and Mefloquine in the NMRI mouse

| Preparation | dose mg/kg (5 ×) | dose ratio | observed values | | | | | | | | | | x̄, s | prolonged s.t. x̄(prep.) - x̄(IC) |
|---|---|---|---|---|---|---|---|---|---|---|---|---|---|---|
| Floxacrine | 1.25 | | 13 | 14 | 14 | 16 | 17 | 19 | 20 | 21 | 22 | 28 | 18.4 ± 4.6 | 11 |
| | 0.62 | | 8 | 9 | 10 | 10 | 10 | 11 | 11 | 11 | 13 | 14 | 10.7 ± 1.8 | 3.3 |
| | 0.312 | | 8 | 8 | 9 | 9 | 9 | 9 | 9 | 9 | 12 | 12 | 9.4 ± 1.4 | 2 |
| Mefloquine | 3.12 | | 13 | 13 | 17 | 17 | 17 | 21 | 21 | 22 | 28 | 28 | 19.7 ± 5.4 | 12.3 |
| (hydrochloride) | 1.56 | | 6 | 6 | 8 | 8 | 8 | 8 | 8 | 8 | 11 | 11 | 8.2 ± 1.7 | 0.8 |
| Floxacrine/ | 1.25/1.56 | 1:1.25 | 15 | 16 | 28 | 28 | 28 | 28 | 28 | 28 | 28 | 28 | 25.5 ± 5.3 | 18.1 |
| Mefloquine | 0.62/3.12 | 1:5 | 24 | 28 | 28 | 28 | 28 | 28 | 28 | 28 | 28 | 28 | 27.6 ± 1.3 | 20.2 |
| | 0.312/3.12 | 1:10 | 15 | 15 | 27 | 27 | 27 | 27 | 27 | 27 | 28 | 28 | 24.8 ± 5.2 | 17.4 |
| untreated, infected control animals | — | — | 6 | 7 | 7 | 7 | 7 | 7 | 8 | 8 | 8 | 9 | 7.4 ± 0.8 | — |

TABLE 4

Synergistic action (over-additive section of the survival time in % - cf. FIG. 4) on blood forms of *Plasmodium berghei* (drug-sensitive strain) after application of compositions containing Floxacrine and Primaquine in the NMRI mouse

| Preparation | dose mg/kg (5 ×) | dose ratio | observed values | | | | | | | | | | x̄, s | prolonged s.t. x̄(prep.) - x̄(IC) |
|---|---|---|---|---|---|---|---|---|---|---|---|---|---|---|
| Floxacrine | 2.5 | | 12 | 14 | 16 | 19 | 20 | 28 | 28 | 28 | 28 | 28 | 22.1 ± 6.6 | 13.8 |
| | 1.25 | | 8 | 8 | 12 | 12 | 13 | 13 | 14 | 16 | 17 | 17 | 13 ± 3.2 | 4.7 |
| | 0.62 | | 7 | 7 | 7 | 7 | 8 | 8 | 9 | 9 | 10 | 10 | 8.2 ± 1.2 | −0.1 |
| Primaquine | 12.5 | | 10 | 13 | 13 | 13 | 14 | 15 | 24 | 28 | 28 | 28 | 18.6 ± 7.4 | 10.3 |
| (diphosphate) | 6.25 | | 10 | 10 | 10 | 10 | 10 | 10 | 11 | 11 | 12 | 12 | 10.6 ± 0.8 | 2.3 |
| | 3.12 | | 7 | 7 | 8 | 8 | 8 | 8 | 9 | 9 | 11 | 11 | 8.6 ± 1.4 | 0.3 |
| Floxacrine/ | 2.5/6.25 | 1:2.5 | 28 | 28 | 28 | 28 | 28 | 28 | 28 | 28 | 28 | 28 | 28 ± 0 | 19.7 |
| Primaquine | 2.5/3.12 | 1:1.25 | 28 | 28 | 28 | 28 | 28 | 28 | 28 | 28 | 28 | 28 | 28 ± 0 | 19.7 |
| | 1.25/12.5 | 1:10 | 28 | 28 | 28 | 28 | 28 | 28 | 28 | 28 | 28 | 28 | 28 ± 0 | 19.7 |
| | 1.25/6.25 | 1:5 | 28 | 28 | 28 | 28 | 28 | 28 | 28 | 28 | 28 | 28 | 28 ± 0 | 19.7 |
| | 1.25/3.12 | 1:2.5 | 28 | 28 | 28 | 28 | 28 | 28 | 28 | 28 | 28 | 28 | 28 ± 0 | 19.7 |
| | 0.62/12.5 | 1:20 | 28 | 28 | 28 | 28 | 28 | 28 | 28 | 28 | 28 | 28 | 28 ± 0 | 19.7 |
| | 0.62/6.25 | 1:10 | 10 | 10 | 12 | 12 | 12 | 12 | 13 | 13 | 17 | 17 | 12.8 ± 2.4 | 4.5 |
| | 0.62/3.12 | 1:5 | 8 | 8 | 9 | 9 | 11 | 11 | 12 | 12 | 13 | 13 | 10.6 ± 2 | 2.3 |
| untreated, infected control animals | — | — | 7 | 8 | 8 | 8 | 8 | 8 | 9 | 9 | 9 | 9 | 8.3 ± 0.7 | — |

TABLE 5

Synergistic action (over-additive section of the survival time in % - cf. FIG. 5) on blood forms of *Plasmodium berghei* (drug-sensitive strain) after application of compositions containing Floxacrine and Pyrimethamine in the NMRI mouse

| Preparation | dose mg/kg (5 ×) | dose ratio | observed values | | | | | | | | | | x̄, s | prolonged s.t. x̄(prep.) - x̄(IC) |
|---|---|---|---|---|---|---|---|---|---|---|---|---|---|---|
| Floxacrine | 2.5 | | 13 | 13 | 13 | 13 | 14 | 14 | 19 | 19 | 28 | 28 | 17.4 ± 6.1 | 7.8 |
| | 1.25 | | 8 | 8 | 9 | 9 | 11 | 11 | 12 | 12 | 13 | 13 | 10.8 ± 2.3 | 1.2 |
| | 0.62 | | 8 | 8 | 8 | 9 | 9 | 10 | 11 | 11 | 13 | 13 | 10 ± 1.9 | 0.4 |
| Pyrimethamine | 0.94 | | 13 | 13 | 14 | 14 | 15 | 15 | 16 | 16 | 28 | 28 | 17.2 ± 5.8 | 7.6 |
| | 0.47 | | 10 | 10 | 13 | 13 | 13 | 14 | 15 | 16 | 23 | 28 | 15.5 ± 5.7 | 5.9 |
| | 0.24 | | 9 | 9 | 10 | 10 | 11 | 11 | 11 | 12 | 12 | 12 | 10.7 ± 1.2 | 1.1 |
| | 0.12 | | 6 | 9 | 9 | 9 | 10 | 11 | 11 | 11 | 13 | 13 | 10.2 ± 2.1 | 0.6 |
| | 2.5/0.24 | 10.42:1 | 16 | 16 | 19 | 19 | 24 | 24 | 28 | 28 | 28 | 28 | 23 ± 5.1 | 13.4 |
| | 2.5/0.12 | 20.83:1 | 15 | 15 | 16 | 16 | 16 | 16 | 28 | 28 | 28 | 28 | 20.6 ± 6.4 | 11 |

TABLE 5-continued

Synergistic action (over-additive section of the survival time in % - cf. FIG. 5) on blood forms of *Plasmodium berghei* (drug-sensitive strain) after application of compositions containing Floxacrine and Pyrimethamine in the NMRI mouse

| Preparation | dose mg/kg (5 ×) | dose ratio | observed values | | | | | | | | | | $\bar{x}, s$ | prolonged s.t. $\bar{x}$(prep.) - $\bar{x}$(IC) |
|---|---|---|---|---|---|---|---|---|---|---|---|---|---|---|
| Floxacrine/ | 1.25/0.94 | 1.33:1 | 15 | 16 | 17 | 18 | 28 | 28 | 28 | 28 | 28 | 28 | 23.4 ± 6 | 13.8 |
| Pyrimethamine | 1.25/0.47 | 2.66:1 | 14 | 14 | 15 | 15 | 17 | 17 | 28 | 28 | 28 | 28 | 20.4 ± 6.6 | 10.8 |
|  | 1.25/0.24 | 5.21:1 | 10 | 12 | 15 | 15 | 15 | 15 | 17 | 17 | 24 | 24 | 16.4 ± 4.5 | 6.8 |
|  | 1.25/0.12 | 10.42:1 | 12 | 12 | 13 | 13 | 15 | 15 | 15 | 15 | 16 | 16 | 14.2 ± 1.6 | 4.6 |
|  | 0.62/0.94 | 1:1.5 | 14 | 15 | 28 | 28 | 28 | 28 | 28 | 28 | 28 | 28 | 25.3 ± 5.7 | 15.7 |
| untreated, infected control animals | — | — | 6 | 7 | 9 | 9 | 9 | 10 | 10 | 11 | 12 | 13 | 9.6 ± 2.1 | — |

TABLE 6

Synergistic action (over-additive section of the survival time in % - cf. FIG. 6) on blood forms of *Plasmodium berghei* (drug-sensitive strain) after application of compositions containing Floxacrine and Cycloguanil in the NMRI mouse

| Preparation | dose mg/kg (5 ×) | dose ratio | observed values | | | | | | | | | | $\bar{x}, s$ | prolonged s.t. $\bar{x}$(prep.) - $\bar{x}$(IC) |
|---|---|---|---|---|---|---|---|---|---|---|---|---|---|---|
| Floxacrine | 1.25 | | 14 | 14 | 19 | 19 | 20 | 20 | 22 | 22 | 28 | 28 | 20.6 ± 4.8 | 13.1 |
|  | 0.625 | | 9 | 9 | 10 | 10 | 10 | 10 | 11 | 11 | 14 | 14 | 10.8 ± 1.8 | 3.3 |
| Cycloguanil | 177.2 | | 7 | 7 | 9 | 9 | 12 | 12 | 13 | 13 | 28 | 28 | 13.8 ± 7.8 | 6.3 |
| pamoate | 88.6 | | 7 | 7 | 8 | 8 | 8 | 8 | 8 | 8 | 9 | 9 | 8 ± 0.7 | 0.5 |
|  | 44.3 | | 7 | 7 | 7 | 7 | 8 | 8 | 9 | 9 | 10 | 10 | 8.2 ± 1.2 | 0.7 |
| Floxacrine/ | 1.25/88.6 | 1:71 | 23 | 24 | 28 | 28 | 28 | 28 | 28 | 28 | 28 | 28 | 27.1 ± 1.9 | 19.6 |
| Cycloguanil | 1.25/44.3 | 1:35 | 28 | 28 | 28 | 28 | 28 | 28 | 28 | 28 | 28 | 28 | 28 ± 0 | 20.5 |
|  | 0.625/177.2 | 1:284 | 17 | 17 | 22 | 22 | 23 | 23 | 28 | 28 | 28 | 28 | 23.6 ± 4.4 | 16.1 |
|  | 0.625/88.6 | 1:142 | 13 | 13 | 14 | 14 | 19 | 19 | 19 | 19 | 23 | 23 | 17.6 ± 3.9 | 10.1 |
|  | 0.625/44.3 | 1:71 | 13 | 13 | 13 | 13 | 16 | 16 | 17 | 17 | 17 | 17 | 15.2 ± 1.9 | 7.7 |
| untreated, infected control animals | — | — | 6 | 7 | 7 | 7 | 7 | 8 | 8 | 8 | 8 | 9 | 7.5 ± 0.9 | — |

TABLE 7

Synergistic action (over-additive section of the survival time in % - cf. FIG. 7) on blood forms of *Plasmodium berghei* (drug-sensitive strain) after application of compositions containing Floxacrine and Trimethoprim in the NMRI mouse

| Preparation | dose mg/kg (5 ×) | dose ratio | observed values | | | | | | | | | | $\bar{x}, s$ | prolonged s.t. $\bar{x}$(prep.) - $\bar{x}$(IC) |
|---|---|---|---|---|---|---|---|---|---|---|---|---|---|---|
| Floxacrine | 2.5 | | 21 | 21 | 23 | 23 | 23 | 23 | 25 | 25 | 26 | 26 | 23.6 ± 1.8 | 15.6 |
|  | 1.25 | | 9 | 9 | 12 | 12 | 12 | 12 | 15 | 15 | 16 | 16 | 12.8 ± 2.6 | 4.6 |
| Trimethoprim | 100 | | 8 | 8 | 8 | 8 | 9 | 9 | 9 | 9 | 10 | 10 | 8.8 ± 0.8 | 0.8 |
|  | 50 | | 7 | 7 | 7 | 7 | 9 | 9 | 10 | 10 | 11 | 11 | 8.8 ± 1.7 | 0.8 |
|  | 25 | | 7 | 7 | 7 | 7 | 9 | 9 | 10 | 10 | 11 | 11 | 8.7 ± 1.6 | 0.7 |
| Floxacrine/ | 2.5/100 | 1:40 | 23 | 23 | 28 | 28 | 28 | 28 | 28 | 28 | 28 | 28 | 27 ± 2.1 | 19 |
| Trimethoprim | 2.5/50 | 1:20 | 20 | 20 | 28 | 28 | 28 | 28 | 28 | 28 | 28 | 28 | 26.4 ± 3.4 | 18.4 |
|  | 2.5/25 | 1:10 | 20 | 20 | 22 | 22 | 28 | 28 | 28 | 28 | 28 | 28 | 25.2 ± 3.7 | 17.2 |
|  | 1.25/100 | 1:80 | 13 | 13 | 15 | 15 | 16 | 16 | 17 | 17 | 17 | 17 | 15.6 ± 1.6 | 7.6 |
|  | 1.25/50 | 1:40 | 13 | 13 | 13 | 13 | 15 | 15 | 15 | 16 | 17 | 17 | 14.7 ± 1.6 | 6.7 |
|  | 1.25/25 | 1:20 | 11 | 11 | 13 | 13 | 14 | 14 | 17 | 17 | 17 | 17 | 14.4 ± 2.5 | 6.4 |
| untreated, infected control animals | — | — | 6 | 6 | 6 | 7 | 8 | 9 | 9 | 9 | 10 | 10 | 8 ± 1.6 | — |

TABLE 8

Synergistic action (over-additive section of the survival time in % - cf. FIG. 8) on blood forms of *Plasmodium berghei* (drug-sensitive strain) after application of compositions containing Floxacrine and Sulfadoxine in the NMRI mouse

| Preparation | dose mg/kg (5 ×) | dose ratio | observed values | | | | | | | | | | $\bar{x}, s$ | prolonged s.t. $\bar{x}$(prep.) - $\bar{x}$(IC) |
|---|---|---|---|---|---|---|---|---|---|---|---|---|---|---|
| Floxacrine | 2.5 | | 14 | 14 | 14 | 15 | 16 | 16 | 18 | 23 | 28 | 28 | 18.6 ± 5.6 | 10.8 |
|  | 1.875 | | 13 | 13 | 14 | 14 | 15 | 15 | 16 | 19 | 26 | 28 | 17.3 ± 5.4 | 9.5 |
|  | 1.25 | | 8 | 9 | 11 | 12 | 12 | 12 | 14 | 14 | 15 | 15 | 12.2 ± 2.4 | 4.4 |

TABLE 8-continued

Synergistic action (over-additive section of the survival time in % - cf. FIG. 8) on blood forms of *Plasmodium berghei* (drug-sensitive strain) after application of compositions containing Floxacrine and Sulfadoxine in the NMRI mouse

| Preparation | dose mg/kg (5 ×) | dose ratio | observed values | | | | | | | | | $\bar{x}, s$ | prolonged s.t. $\bar{x}$(prep.) - $\bar{x}$(IC) |
|---|---|---|---|---|---|---|---|---|---|---|---|---|---|
| | 0.625 | | 6 | 7 | 7 | 8 | 9 | 9 | 9 | 9 | 10 | 11 8.5 ± 1.5 | 0.7 |
| Sulfadoxine | 20 | | 13 | 14 | 14 | 15 | 17 | 17 | 19 | 28 | 28 | 28 19.3 ± 6.3 | 11.5 |
| | 10 | | 13 | 14 | 15 | 16 | 17 | 20 | 23 | 23 | 28 | 28 19.7 ± 5.6 | 11.9 |
| | 7.5 | | 12 | 12 | 12 | 13 | 14 | 15 | 16 | 24 | 28 | 28 17.4 ± 6.6 | 9.6 |
| | 5 | | 11 | 12 | 12 | 12 | 13 | 13 | 14 | 14 | 15 | 17 13.3 ± 1.8 | 5.5 |
| | 2.5 | | 10 | 10 | 10 | 10 | 11 | 11 | 12 | 15 | 15 | 17 12.1 ± 2.6 | 4.3 |
| Floxacrine/ | 2.5/5 | 1:2 | 28 | 28 | 28 | 28 | 28 | 28 | 28 | 28 | 28 | 28 28 ± 0 | 20.2 |
| Sulfadoxine | 2.5/2.5 | 1:1 | 28 | 28 | 28 | 28 | 28 | 28 | 28 | 28 | 28 | 28 28 ± 0 | 20.2 |
| | 1.875/5 | 1:2.67 | 28 | 28 | 28 | 28 | 28 | 28 | 28 | 28 | 28 | 28 28 ± 0 | 20.2 |
| | 1.875/2.5 | 1:1.33 | 20 | 24 | 28 | 28 | 28 | 28 | 28 | 28 | 28 | 28 26.8 ± 2.7 | 19 |
| | 1.25/20 | 1:16 | 28 | 28 | 28 | 28 | 28 | 28 | 28 | 28 | 28 | 28 28 ± 0 | 20.2 |
| | 1.25/10 | 1:8 | 17 | 21 | 28 | 28 | 28 | 28 | 28 | 28 | 28 | 28 26.2 ± 3.9 | 18.4 |
| | 1.25/7.5 | 1:6 | 26 | 26 | 28 | 28 | 28 | 28 | 28 | 28 | 28 | 28 27.6 ± 0.8 | 19.8 |
| | 1.25/5 | 1:4 | 15 | 15 | 17 | 17 | 28 | 28 | 28 | 28 | 28 | 28 23.2 ± 6.2 | 15.4 |
| | 0.625/20 | 1:32 | 14 | 16 | 21 | 24 | 24 | 26 | 28 | 28 | 28 | 28 23.7 ± 5.2 | 15.9 |
| | 0.625/10 | 1:16 | 14 | 15 | 20 | 22 | 23 | 24 | 26 | 26 | 27 | 28 22.5 ± 4.9 | 14.7 |
| untreated, infected control animals | — | — | 7 | 7 | 7 | 7 | 7 | 8 | 8 | 8 | 9 | 10 7.8 ± 1 | — |

TABLE 9

Synergistic action (over-additive section of the survival time in % - cf. FIG. 9) on blood forms of *Plasmodium berghei* (drug-sensitive strain) after application of compositions containing Floxacrine and Dapsone in the NMRI mouse

| Preparation | dose mg/kg (5 ×) | dose ratio | observed values | | | | | | | | | $\bar{x}, s$ | prolonged s.t. $\bar{x}$(prep.) - $\bar{x}$(IC) |
|---|---|---|---|---|---|---|---|---|---|---|---|---|---|
| Floxacrine | 2.5 | | 14 | 14 | 15 | 15 | 16 | 17 | 17 | 27 | 28 | 28 18.1 ± 5.3 | 11.2 |
| | 1.25 | | 8 | 8 | 9 | 9 | 9 | 10 | 11 | 11 | 11 | 14 10 ± 1.8 | 3.1 |
| Dapsone | 100 | | 12 | 13 | 13 | 14 | 15 | 15 | 16 | 16 | 28 | 28 17 ± 5.9 | 10.1 |
| | 50 | | 12 | 12 | 13 | 13 | 13 | 15 | 16 | 18 | 22 | 24 15.8 ± 4.3 | 8.9 |
| | 25 | | 12 | 12 | 13 | 13 | 13 | 15 | 16 | 17 | 19 | 20 15 ± 2.9 | 8.1 |
| | 12.5 | | 12 | 13 | 13 | 13 | 15 | 15 | 15 | 16 | 17 | 14 15.3 ± 3.4 | 8.4 |
| | 6.25 | | 8 | 8 | 8 | 8 | 9 | 10 | 10 | 10 | 11 | 11 9.3 ± 1.3 | 2.4 |
| Floxacrine/ | 2.5/25 | 1:10 | 28 | 28 | 28 | 28 | 28 | 28 | 28 | 28 | 28 | 28 28 ± 0 | 21.1 |
| Dapsone | 2.5/12.5 | 1:5 | 28 | 28 | 28 | 28 | 28 | 28 | 28 | 28 | 28 | 28 28 ± 0 | 21.1 |
| | 1.25/100 | 1:80 | 28 | 28 | 28 | 28 | 28 | 28 | 28 | 28 | 28 | 28 28 ± 0 | 21.1 |
| | 1.25/50 | 1:40 | 28 | 28 | 28 | 28 | 28 | 28 | 28 | 28 | 28 | 28 28 ± 0 | 21.1 |
| | 1.25/25 | 1:20 | 28 | 28 | 28 | 28 | 28 | 28 | 28 | 28 | 28 | 28 28 ± 0 | 21.1 |
| | 1.25/12.5 | 1:10 | 28 | 28 | 28 | 28 | 28 | 28 | 28 | 28 | 28 | 28 28 ± 0 | 21.1 |
| | 1.25/6.25 | 1:5 | 12 | 12 | 13 | 13 | 14 | 14 | 15 | 15 | 28 | 28 16.4 ± 6.2 | 9.5 |
| untreated, infected control animals | — | — | 6 | 6 | 6 | 6 | 7 | 7 | 7 | 7 | 8 | 9 6.9 ± 1 | — |

What is claimed is:

1. An anti-malarial composition containing as the active ingredient a mixture of 7-chloro-10-hydroxy-3-(4-trifluoromethyl-phenyl)-3,4-dihydroacridino-1,9-(2H, 10H)-dione and 7-chloro-4-(diethylamino-1-methylbutylamino)-quinoline (Chloroquine), in a proportion by weight of between 4:1 and 1:20.

2. A method of treating malaria in patients comprising administering to said patient a composition as defined in claim 1 in a total dose of 1.37 to 27.5 mg per kg of body weight.

3. A method of treating malaria in patients comprising administering to said patient a composition as defined in claim 1 in a total dose of 1.56 to 11.25 mg per kg of body weight.

* * * * *